US00PP30612P3

(12) United States Plant Patent
Paduch

(10) Patent No.: US PP30,612 P3
(45) Date of Patent: Jun. 25, 2019

(54) ***RHIPSALIDOPSIS* PLANT NAMED 'BCSU-97.002'**

(50) Latin Name: ***Rhipsalidopsis* hybrid**
Varietal Denomination: BCSU-97.002

(71) Applicant: Bay City Flower Company, Inc., Half Moon Bay, CA (US)

(72) Inventor: Louis Paduch, Carver, MA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 15/731,064

(22) Filed: Apr. 13, 2017

(65) Prior Publication Data

US 2018/0303021 P1 Oct. 18, 2018

(51) Int. Cl.
*A01H 5/02* (2018.01)
*A01H 6/24* (2018.01)

(52) U.S. Cl.
USPC ..... Plt./372
CPC ..... *A01H 6/24* (2018.05)

(58) Field of Classification Search
USPC ..... Plt./372
See application file for complete search history.

*Primary Examiner* — Susan McCormick Ewoldt
*Assistant Examiner* — Karen M Redden
(74) *Attorney, Agent, or Firm* — James R. Cypher; Charles R. Cypher

(57) ABSTRACT

A variety of the Cactaceae family produced by a controlled cross named 'BCSU-97.002'. 'BCSU-97.002' has a strong growth habit, a "red" colored bloom, a strong propensity to branch with minimal pruning, erect stems, and blooming flowers that last for two weeks on the plant.

3 Drawing Sheets

Latin name of genus and species of the plant claimed: *Rhipsalidopsis* hybrid.

Varietal denomination:

The new plant's varietal denomination is 'BCSU-97.002'.

BACKGROUND OF THE INVENTION

The present invention relates to a new and distinct variety of the Cactaceae family. The new variety is a *Rhipsalidopsis* hybrid named 'BCSU-97.002' by the inventor. The inventor is Louis Paduch, a citizen of the United States.

SUMMARY OF THE INVENTION

This new variety was produced by the inventor through a controlled hybridization process from commercial varieties. The parent plants have not been patented or otherwise formally identified.

The flower is multi-toned.

The distinguishing characteristics of the new variety are retained by asexually reproduced, successive generations.

The new variety possesses the desirable characteristics of: a strong growth habit with erect stems; a multi-colored bloom with an orange colored throat—R.H.S. 29B (orange group); relatively large flowers that face upwardly; and a strong propensity to branch with minimal pruning.

Blooming flowers on the plant can last as long as two weeks at temperatures between 60 and 70 degrees Fahrenheit. Cold temperatures slow down the rate at which buds mature into flowers. Strong light is also necessary for bud development.

TABLE 1

| | New Variety BCSU-97.002' | U.S. Plant Pat. No. 27,636 Rhipsalidopsis Plant named 'Beverly' |
|---|---|---|
| Plant height | 8" to 9" | 8" to 9" |
| Phylloclades | 40-50 mm long, 13-25 mm wide, color RHS 139B (green group). Diameter: 5.1 cm. | 40-60 mm long, 13-30 mm wide, color RHS 137A (green group). Diameter: 5.5 cm. |
| Flower Tepals | Up to 32 mm long, tepals are thin and variegated in color on both sides; base of tepals on both the abaxial and adaxial sides is R.H.S. 29B (orange group); color darkens to R.H.S. 48D (red group) at the tops of both the abaxial and adaxial surfaces; abaxial surfaces of the tepals have centered strips of darker pigment that is R.H.S. 50A (red group); tips of the tepals on both the abaxial and adaxial surfaces are also R.H.S. 50A (red group) | Up to 4 cm long, tepals are thin; tepals are uniformly dark above base on both sides. Overall color appearance of tepals is R.H.S. 46B (red group); some tepals become R.H.S. 54 B (red group) |
| Filament Color | Tops of the filaments of the stamens are R.H.S. 41B (red group) and the color fades to R.H.S. 158B (yellow-white group) at the base of the filaments | RHS 74B (red-purple group) |

TABLE 1-continued

| | U.S. Plant Pat. No. 14,423 Rhipsalidopsis Plant named 'Lauren' | U.S. Plant Patent No. 26,473 Rhipsalidopsis plant named 'PKMRHIPS09' |
|---|---|---|
| Plant height | 12 cm | 13 to 15 cm |
| Phylloclades | 20-55 mm long, up to 19 mm wide, color RHS 137C. | 25-35 mm long, up to 24 mm wide, color RHS 146A (yellow-green group). |
| Flower | Diameter: 31-38 mm. | Diameter: up to 7 cm. Length: 4 cm, including ovary. |
| Tepals | 19-25 mm long; tepals are thin and semi-transparent; tepas are darkest at mid-line of tepal, lightening toward margins; overall color appearance is RHS 69A (red-purple group); darkest portions of tepals are R.H.S. 73A (red-purple group), with lighter margins ranging from R.H.S. 62B (red-purple group) to white | Up to 35 mm long, up to 7 mm wide, color RHS 34A (orange-red group) |
| Filament Color | "darker than perianth" | RHS N155C-N155D |

The new variety has been asexually reproduced by the inventor and under the direction of the inventor at a commercial nursery in Half Moon Bay, Calif. The new variety has been asexually reproduced through successive generations by cuttings, and it has been found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
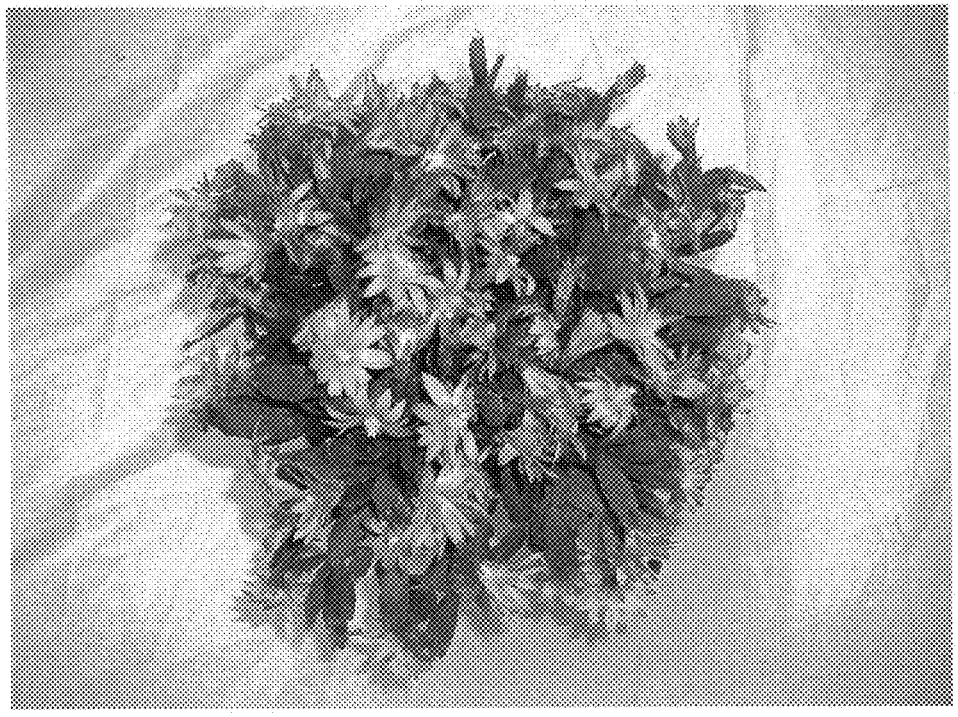
FIG. 1 is a color photograph of several individuals of the new variety illustrating the overall appearance and form of the plants, and the abundance of blooms, when grown in a single pot for commercial sale.
Figure 2:
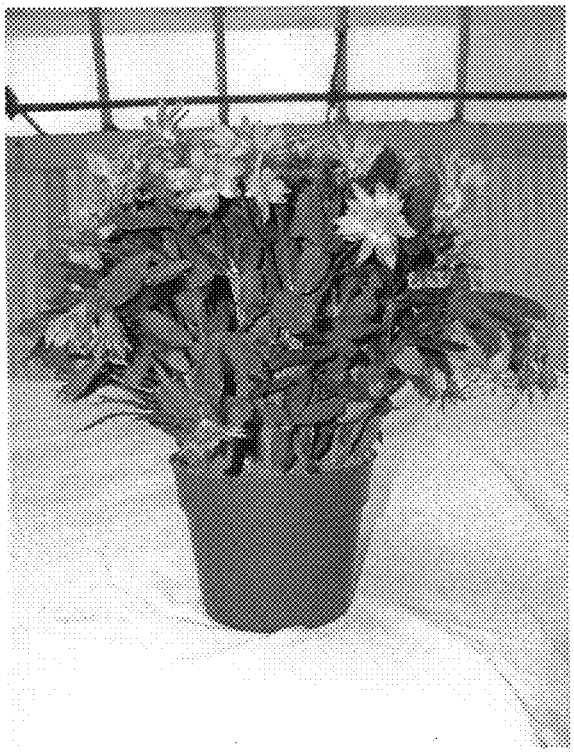
FIG. 2 is a side view, color photograph of several individuals of the new variety illustrating the overall appearance and form of the plants, and the abundance of blooms, when grown in a single pot for commercial sale.
Figure 3:
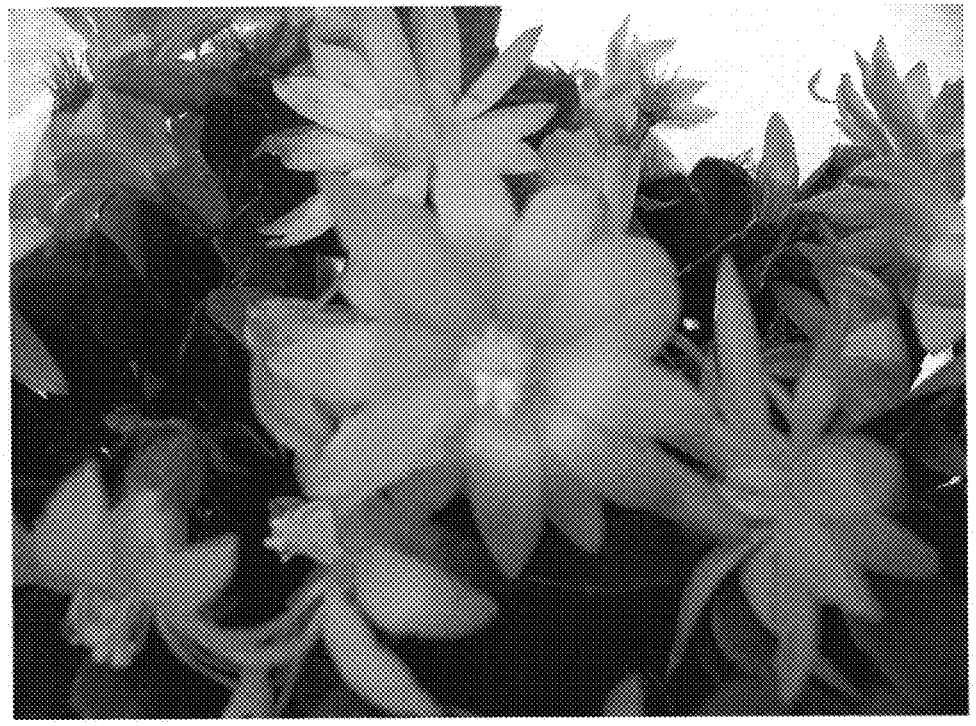
FIG. 3 is color photograph of a several flowers of the new variety.
Figure 4:
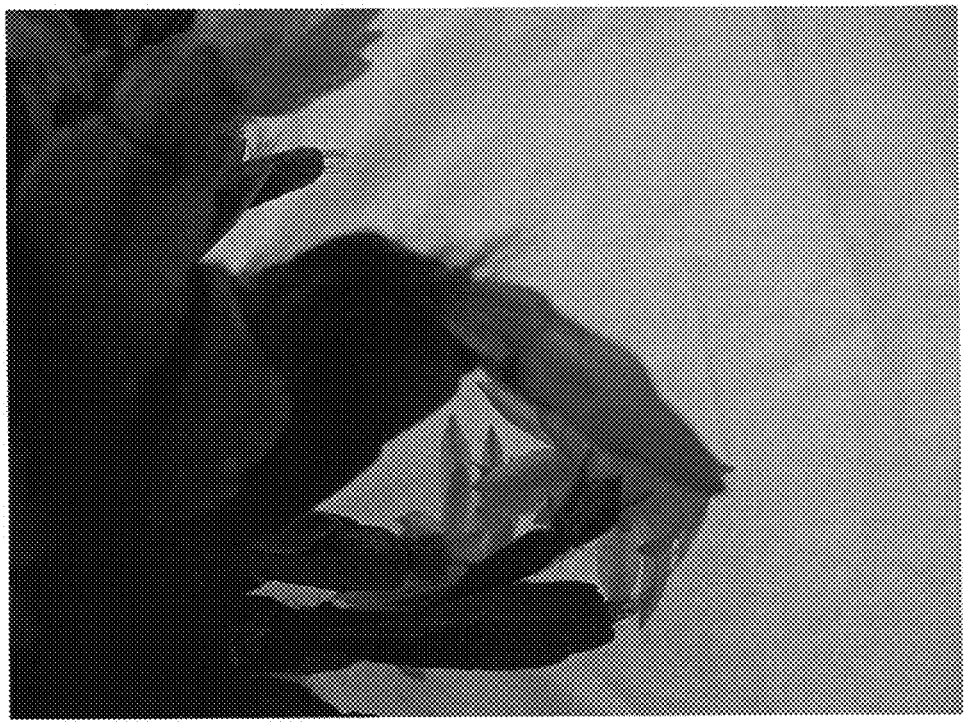
FIG. 4 is a color photograph of the top of a flowering stem of the new variety.
Figure 5:
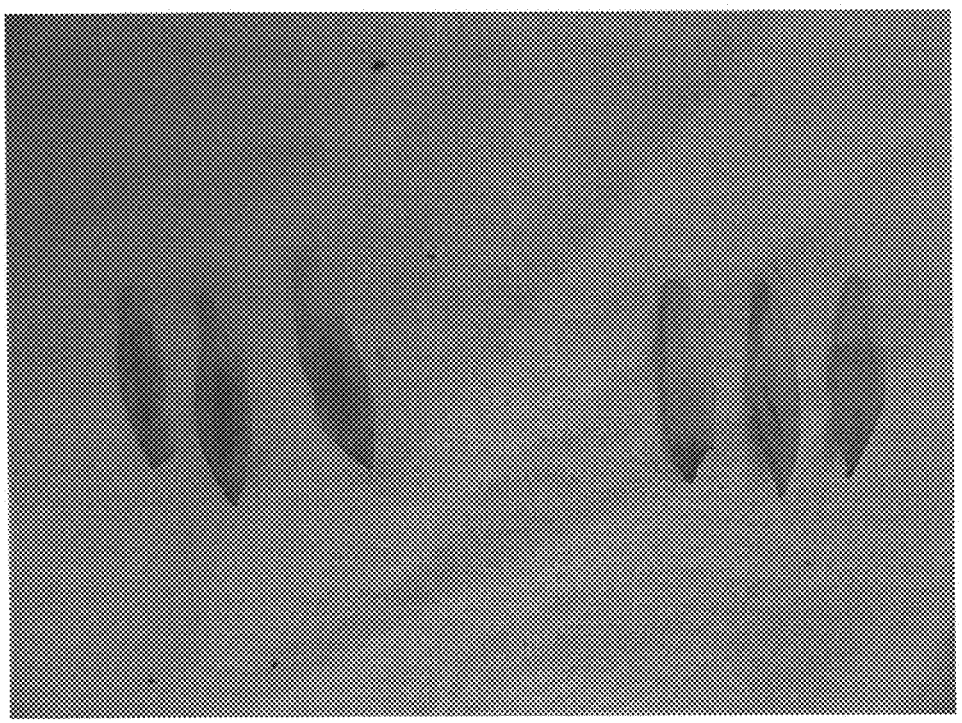
FIG. 5 is a color photograph of the tepals of the new variety.
Figure 6:
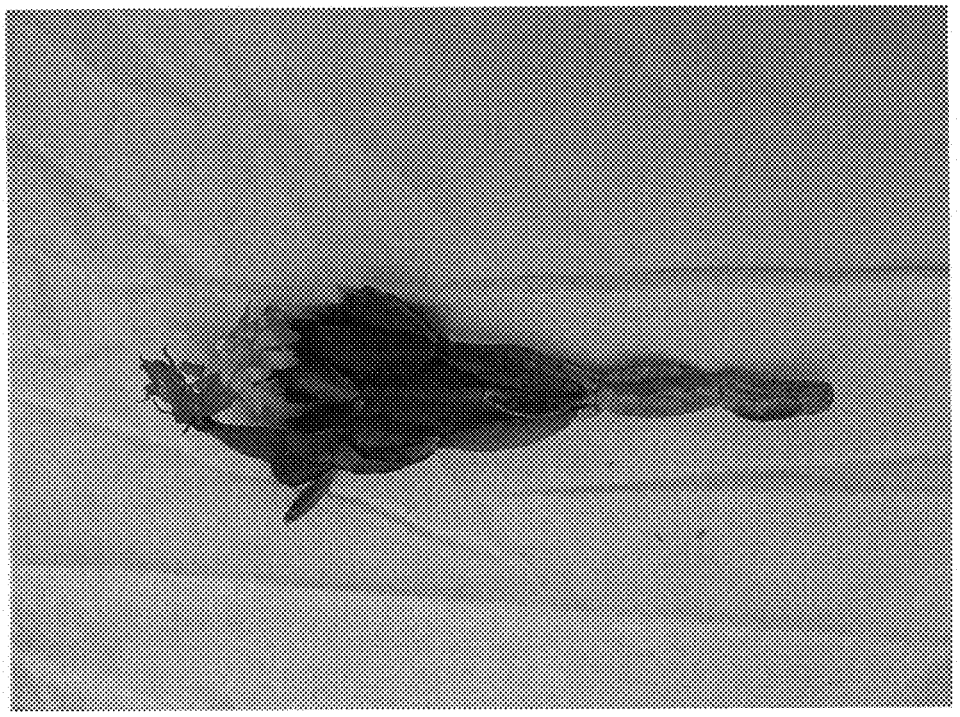
FIG. 6 is a color photograph of one individual plant grown for commercial sale removed from its soil.

The following is a detailed description of the new variety. The new variety has not been observed under all possible environmental conditions. Color designation and other values may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The plants observed were grown in 6" pots. The observed plants are ready for commercial sale.

Multiple cuttings were placed in each pot. Most cuttings had six levels of phylloclades, including the basal phylloclade that was inserted in the dirt, with buds at the top of the highest phylloclades.

The following description is based on observations of optimally fertilized plants.

The plants were started in green houses at a commercial nursery in Half Moon Bay, Calif. Temperatures in Half Moon Bay on average range from 55 to 65 degrees Fahrenheit in the summer months, and from 45 to 55 degrees Fahrenheit in the winter months.

The plants started as cuttings taken as entire phylloclades. Cuttings were dried in flats for four weeks to harden. Multiple cuttings were then placed in the same pot. The cuttings were kept under glass while they were rooting. At night, the plants were kept at an average temperature of approximately 64 degrees Fahrenheit, and during the day, the plants were allowed to get as hot as 75 to 80 degrees Fahrenheit. Cuttings generally take a month to begin producing roots and then another month to fully root.

DETAILED PLANT DESCRIPTION

Varietal name: 'BCSU-97.002'. Classification: Family—Cactaceae. Genus and Species—*Rhipsalidopsis* hybrid. Parentage: un-named individuals that are also *Rhipsalidopsis* hybrids.

Form: Terrestrial, shade-loving, succulent, leafless plant with jointed and branched stems. Stems: General—Irregular stems of multi-branching upright, adventitiously rootable, flattened phylloclades. Plants observed had stems that generally consisted of 6 levels of phylloclades. Their stems branch at multiple levels, usually with 1 to 3 branches growing out of the apex of the phylloclade. The flattened phylloclades have a fairly prominent midrib (especially in phylloclades at the base of mature plants) and weakly toothed lateral wings. The observed plants were 8" to 9" high.

Phylloclades—General: Mature phylloclades are generally oblong, elongated, and flattened with wings, and have a transversely elongated, areole bearing, truncated apex. From the transversely elongated apex, the wing margins generally run straight or taper slightly to the basal portions (or occasionally they flare outwardly somewhat), where they then taper and merge through a pointed, basal juncture with the phylloclade therebelow. The margins of the wings are also weakly toothed or weakly crenate and an axillary areole is associated with each blunt tooth. Immature phylloclades are often not flattened, but four-angled, having multiple ribs terminating at axillary areoles. The apex of the phylloclade is transversely elongated, and areole bearing with compound areoles. The lateral margins typically have 3 to 4 alternately spaced axillary areoles. Midrib: A somewhat prominent midrib extends longitudinally of the phylloclade and continuously through the joints. Texture: Phylloclades have a smooth, waxy epidermis. Wax in basal phylloclades and phylloclades inserted in the ground becoming thick, corky and translucent with age. First phylloclade above basal phylloclade will often have thick corky wax at its base and along up its midrib part way. Size: Phylloclades are usually between 40 mm and 50 mm long, with young phylloclades as short as 20 mm. Phylloclades bearing flowers can be as short as 32 mm long. Phylloclades are generally 4 mm thick at the midrib, and tapering to 1 mm thick at the margins. Phylloclades are generally 13 to 25 mm at their widest point. Color: Mature phylloclades are R.H.S. 139B (green group) while immature phylloclades are a brighter green: R.H.S. 143A (green group). Some phylloclades can have dark margins, with the midrib and base of the phylloclade being lighter. Areoles: Terminal areole—Large, compound, elongated, oval-shaped with several acicular bristles, and several buds that may mature into either new phylloclades or flowers. The opposite ends of the areole are located adjacent to subsidiary areoles which are in turn located at the axils of the uppermost blunt teeth located at the distal ends of the phylloclade. The acicular bristles are mostly upright (some bent) bristles in clumps which can be as long as 9 mm and as short as 2 mm. Mature bristles are R.H.S. 177A (greyed-orange group). Axiallary areoles—Typically there are 3 axial areoles on each side of the phylloclade. Typically these areoles have no or very minute acicular bristles without glochidia Blunt teeth are also found with the axiallary areoles.

Buds: General—Unarmored and ovoid. Color of tepals of buds are generally R.H.S. 47 B (red group). From 1 to 6 flower buds can form on the elongated terminal areole of the uppermost phylloclades. Most of the buds on the uppermost phylloclades will fall off the plant before the flowers bloom; however, when the plant is in full bloom it is common for the uppermost phylloclade to have only 1 flower. No buds on the second highest phylloclade of a branch.

Flowers: General—Sessile, actinomorphic, terminal, perfect and epigynous with tepals (undifferentiated whorled sepals and petals) having a spiral emergence as a perianth. Perianth, androecium and gynoecium will wither attached to the ovary. Perianth—General: Free, whorled tepals inserted on top of the ovary. Tepals become more reflexed as the flower ages. When the flower is mature there are often 5 very small sepals whose color is from R.H.S 47 B (red group). As many as 20 tepals on a flower. Shape: Lanceolate with entire margins and very acute tips. Texture: Glabrous. Size: Largest tepals of mature flower is 32 mm. Fully opened flower generally has a diameter of 5.1 cm. Color: Tepals are thin. Tepals are variegated in color on both sides. The base of tepals on both the abaxial and adaxial sides is R.H.S. 29B (orange group). The color of the tepals darkens to R.H.S. 48D (red group) at the tops of both the abaxial and adaxial surfaces. The abaxial surfaces of the tepals have centered strips of darker pigment that is R.H.S. 50A (red group). The tips of the tepals on both the abaxial and adaxial surfaces are also R.H.S. 50A (red group). Androecium (stamens).—General: Numerous stamens (often more than 70) with outermost stamens having filaments basally fused to the perianth. Filaments are basally attached to the anther. Stamens are inserted with respect to the sepals, but become exserted as the tepals become reflexed. Pollen color: R.H.S. 7 A (yellow group). Texture: Filament is glabrous. Size: Stamen filaments are approximately 5 to 15 mm long, and the anthers are approximately 1 mm long. Color: the tops of the stamens are R.H.S. 41B (red group) and the color fades to R.H.S. 158B (yellow-white group) at the base of the stamens. Gynoecium (pistil).—General: Compound ovary with parietal placentation (generally 5 carpels), having a united style, that is of equal length as largest stamens, and inserted in tepals, but becoming exserted as tepals become reflexed. Style: R.H.S 158C (yellow-white group) at base with R.H.S. 49D (red group) below. Length: 12 mm. Texture: glabrous. Stigma: Erect and becomes reflexed as it ages with usually 5 lobes (but there can be as many as 8 lobes) Color: R.H.S. 158 C (yellow-white group) on the abaxial side. Ovary: General—Compound ovary with a single cavity and parietal placentation and generally 5 carpels, with numerous ovules. The ovary is inferior and obovate to terete with five angles and generally broadening from insertion to floral end. Generally, mature ovaries have a diameter of about 7 mm. Color—two colors—ribs are a R.H.S. 53 A (red group) and between the ribs the ovary is R.H.S. 147 B (yellow-green group).

Bloom life.—Two to three weeks when forced.

Fruit.—General: ovaries wither and fall from phylloclades with flower.

I claim:

1. The new and distinct *Rhipsalidopsis* hybrid plant of the Cactaceae family substantially as herein shown and described.

* * * * *